US011001618B2

(12) United States Patent
Kume et al.

(10) Patent No.: US 11,001,618 B2
(45) Date of Patent: May 11, 2021

(54) OVEREXPRESSION OF FOXC1 TO TREAT CORNEAL VASCULARIZATION

(71) Applicants: Northwestern University, Evanston, IL (US); The Governors of the University of Alberta, Edmonton (CA)

(72) Inventors: Tsutomu Kume, Wilmette, IL (US); Ordan Lehmann, Edmonton (CA)

(73) Assignees: Northwestern University, Evanston, IL (US); The Governors of the University of Alberta, Edmonton (CA)

( * ) Notice: Subject to any disclaimer, the term of this patent is extended or adjusted under 35 U.S.C. 154(b) by 40 days.

(21) Appl. No.: 16/278,438

(22) Filed: Feb. 18, 2019

(65) Prior Publication Data

US 2019/0270782 A1 Sep. 5, 2019

Related U.S. Application Data

(60) Provisional application No. 62/637,795, filed on Mar. 2, 2018.

(51) Int. Cl.
| | |
|---|---|
| *C07K 14/475* | (2006.01) |
| *A61K 48/00* | (2006.01) |
| *A61P 9/00* | (2006.01) |
| *A61P 9/10* | (2006.01) |
| *A61P 27/02* | (2006.01) |
| *C07K 14/47* | (2006.01) |
| *A61K 9/00* | (2006.01) |

(52) U.S. Cl.
CPC .......... *C07K 14/475* (2013.01); *A61K 9/0019* (2013.01); *A61K 9/0048* (2013.01); *A61K 48/0016* (2013.01); *A61K 48/0058* (2013.01); *A61K 48/0075* (2013.01); *A61P 9/10* (2018.01); *A61P 27/02* (2018.01); *C07K 14/4702* (2013.01)

(58) Field of Classification Search
None
See application file for complete search history.

(56) References Cited

U.S. PATENT DOCUMENTS

| 4,458,066 A | 7/1984 | Caruthers |
| 4,683,195 A | 7/1987 | Mullis |
| 4,683,202 A | 7/1987 | Mullis |
| 5,494,810 A | 2/1996 | Barany |
| 7,396,664 B2 | 7/2008 | Daly |

FOREIGN PATENT DOCUMENTS

| WO | WO-2006074430 A2 * | 7/2006 | ......... G01N 33/5743 |
| WO | 2015061779 | 4/2015 | |

OTHER PUBLICATIONS

Seungwoon Seo, Hardeep P. Singh, Pedro M. Lacal, Amy Sasman, Anees Fatima, Ting Liu, Kathryn M. Schultz, Douglas W. Losordo, Ordan J. Lehmann, and Tsutomu Kume. Forkhead box transcription factor FoxC1 preserves corneal transparency by regulating vascular growth. PNAS Feb. 7, 2012 109 (6) 2015-2020 (Year: 2012).*
Fred B. Berry, Megan A. O'Neill, Miguel Coca-Prados, and Michael A. Walter. FOXC1 Transcriptional Regulatory Activity Is Impaired by PBX1 in a Filamin A-Mediated Manner. Molecular and Cellular Biology, Feb. 2005, p. 1415-1424. (Year: 2005).*
Rajiv R. Mohan, Jason T. Rodier, and Ajay Sharma. Corneal Gene Therapy: Basic Science and Translational Perspective. Ocul Surf. Jul. 2013; 11(3): 150-164. (Year: 2013).*
Janine Davis, Joram Piatigorsky. Overexpression of Pax6 in Mouse Cornea Directly Alters Corneal Epithelial Cells: Changes in Immune Function, Vascularization, and Differentiation. Investigative Ophthalmology & Visual Science, Jun. 2011, vol. 52, No. 7: 4158-4168. (Year: 2011).*
Kazuo Tsuboto et al., Adenovirus-Mediated Gene Transfer to the Ocular Surface Epithelium, Exp. Eye Res. 67, 531-538 (Year: 1998).*
Kelly M. Stewart, Kristin L. Horton, and Shana O. Kelley. Cell-penetrating peptides as delivery vehicles for biology and medicine. Org. Biomol. Chem., 2008, 6, 2242-2255. (Year: 2008).*
Mohan et al. (2011) Targeted Decorin Gene Therapy Delivered with Adeno-Associated Virus Effectively Retards Corneal Neovascularization In Vivo. PLOS ONE, 6(10):e26432, pp. 1-11 (Year: 2011).*
NP_001444.2 (Forkhead box protein C1 amino acid sequence, NCBI Reference Sequence, priority to Jan. 30, 2017, 4 pages) (Year: 2017).*
Mirzayans et al. (1995) Mutation of the PAX6 Gene in Patients with Autosomal Dominant Keratitis. American Journal of Human Genetics, 57:539-548 (Year: 1995).*
Kabza et al. (2017) Collagen synthesis disruption and downregulation of core elements of TGF-β, Hippo, and Wnt pathways in keratoconus corneas. European Journal of Human Genetics, 25:582-590 (Year: 2017).*
Regenfuss et al., Corneal (lymph)angiogenesis—from bedside to bench and back: a tribute to Judah Folkman. Lymphat Res Biol. 2008;6(3-4):191-201.
Saleem, R. A., et al. "Analyses of the effects that disease-causing missense mutations have on the structure and function of the winged-helix protein FOXC1." The American Journal of Human Genetics 68.3 (2001): 627-641.
Saleem, R. A., et al. "Essential structural and functional determinants within the forkhead domain of FOXC1." Nucleic acids research 32.14 (2004): 4182-4193.
Saleem, R. A., et al. "Identification and analysis of a novel mutation in the FOXC1 forkhead domain." Investigative ophthalmology & visual science 44.11 (2003): 4608-4612.

(Continued)

*Primary Examiner* — Neil P Hammell
(74) *Attorney, Agent, or Firm* — Quarles & Brady LLP

(57) ABSTRACT

Disclosed are methods and pharmaceutical compositions for treating and inhibiting conical vascularization including conical vascularization associated with viral infection, chemical injury, autoimmune conditions, and post-corneal transplantation or in subjects having a PAX6 mutation associated with conical vascularization. The methods and pharmaceutical compositions are utilized in administering treatment that results in increased concentration of FOXC1 in a subject's cornea in order to treat or inhibit corneal vascularization.

3 Claims, 4 Drawing Sheets

Specification includes a Sequence Listing.

(56) References Cited

OTHER PUBLICATIONS

Saleem, R. A., et al. "Structural and functional analyses of disease-causing missense mutations in the forkhead domain of FOXC1." Human molecular genetics 12.22 (2003): 2993-3005.
Seifi, M., et al. "Comparison of bioinformatics prediction, molecular modeling, and functional analyses of FOXC1 mutations in patients with Axenfeld-Rieger syndrome." Human mutation 38.2 (2017): 169-179.
Seo et al., "Forkhead box transcription factor FoxC1 preserves corneal transparency by regulating vascular growth." Proc Natl Acad Sci U S A. 2012;109(6):2015-20.
Sharma, A., et al. "AAV serotype influences gene transfer in corneal stroma in vivo." Experimental eye research 91.3 (2010):440-448.
Suzuki, T., et al. "A novel (Pro79Thr) mutation in the FKHL7 gene in a Japanese family with Axenfeld-Rieger syndrome." American journal of ophthalmology 132.4 (2001): 572-575.
Tatusova, TA et al. (1999), "Blast 2 sequences—a new tool for comparing protein and nucleotide sequences", FEMS Microbiol Lett. 174:247-250.
Tumer et al., Axenfeld-Rieger syndrome and spectrum of PITX2 and FOXC1 mutations. Eur J Hum Genet. 2009;17(12):1527-39.
Weisschuh, N., et al. "Novel mutations of FOXC1 and PITX2 in patients with Axenfeld-Rieger malformations." Investigative ophthalmology & visual science 47.9 (2006): 3846-3852.
Wetmur, J. G. "DNA probes: applications of the principles of nucleic acid hybridization." Critical reviews in biochemistry and molecular biology 26.3-4 (1991): 227-259.
Zhao, D. et al. "Inhibition of Traumatic and Genetic Models of Corneal Vascularization with Overexpression of FOXC1" Poster presented at Cornea and Ocular Surface Biology and Pathology Conference. Feb. 16, 2018.
Altschul, S. F. et al. "Basic local alignment search tool." Journal of molecular biology 215.3 (1990): 403-410.
Alward WL. Axenfeld-Rieger syndrome in the age of molecular genetics. Am J Ophthalmol. 2000;130(1):107-15.
Anderson C, et al. An alkali-burn injury model of corneal neovascularization in the mouse. J Vis Exp. 2014(86). PMID:24748032.
Anonymous. Blindness Breakthrough. Article. Folio.ca. Dec. 13, 2011. Available online at https://www.folio.ca/blindness-breakthrough/.
Baulmann DC, et al. Pax6 heterozygous eyes show defects in chamber angle differentiation that are associated with a wide spectrum of other anterior eye segment abnormalities. Mech Dev. 2002;118(1-2):3-17.
Beaucage, S. L., et al. (1981). Deoxynucleoside phosphoramidities—a new class of key intermediates for deoxypolynucleotide synthesis. Tetrahedron Letters, 22(20), 1859-1862.
Berry, F. B., et al. "Functional interactions between FOXC1 and PITX2 underlie the sensitivity to FOXC1 gene dose in Axenfeld-Rieger syndrome and anterior segment dysgenesis." Human molecular genetics 15.6 (2006): 905-919.
Berry, F. B., et al. "Regulation of FOXC1 stability and transcriptional activity by an epidermal growth factor-activated mitogen-activated protein kinase signaling cascade." Journal of Biological Chemistry 281.15 (2006): 10098-10104.
Berry, F. B., et al. (2002). FOXC1 transcriptional regulation is mediated by N-and C-terminal activation domains and contains a phosphorylated transcriptional inhibitory domain. Journal of Biological Chemistry, 277(12), 10292-10297.
Bin, L., et al. "Forkhead box C1 regulates human primary keratinocyte terminal differentiation." PloS one 11.12 (2016):e0167392.
Brown, E. L., et al. "[8] Chemical synthesis and cloning of a tyrosine tRNA gene." Methods in Enzymology. vol. 68. Academic Press, 1979. 109-151.
Chang, TC et al. "Axenfeld-Rieger syndrome: new perspectives." Br J Ophthalmol. 2012;96(3):318-22.
Colella P, et al. Emerging Issues in AAV-Mediated In Vivo Gene Therapy. Mol Ther Methods Clin Dev. 2018;8:87-104. Posted online Dec. 1, 2017.

Derakhshankhah, H. et al. "Cell penetrating peptides: A concise review with emphasis on biomedical applications." Biomedicine & Pharmacotherapy 108 (2018): 1090-1096.
Du, R.-F., et al. "A novel mutation of FOXC1 (R127L) in an Axenfeld-Rieger syndrome family with glaucoma and multiple congenital heart diseases." Ophthalmic genetics 37.1 (2016): 111-115.
Feizi S. et al., "Therapeutic approaches for corneal neovascularization." Eye Vis (Lond). 2017;4:28.
Fetterman, C. D., et al. "Characterization of a novel FOXC1 mutation, P297S, identified in two individuals with anterior segment dysgenesis." Clinical genetics 76.3 (2009): 296-299.
Fuse, N, et al. "Novel mutations in the FOXC1 gene in Japanese patients with Axenfeld-Rieger syndrome." Molecular vision 13 (2007): 1005.
Goodchild, J. "Conjugates of oligonucleotides and modified oligonucleotides: a review of their synthesis and properties." Bioconjugate Chemistry 1.3 (1990): 165-187.
Gripp, K. W., et al. "Cardiac anomalies in Axenfeld-Rieger syndrome due to a novel FOXC1 mutation." American Journal of Medical Genetics Part a 161.1 (2013): 114-119.
Gupta, D, et al., "Treatments for corneal neovascularization: a review." Cornea. 2011;30(8):927-38.
Hill, R. E., et al. "Mouse small eye results from mutations in a paired-like homeobox-containing gene." Nature 354.6354 (1991): 522-525.
Honkanen, Robert A., et al. "A family with Axenfeld-Rieger syndrome and Peters anomaly caused by a point mutation (Phe112Ser) in the FOXC1 gene." American journal of ophthalmology 135.3 (2003): 368-375.
International Searching Authority. International Search Report and Written Opinion for application PCT/US2019/018408. dated May 16, 2019.
Ito, Y. A., et al. "Analyses of a novel L130F missense mutation in FOXC1." Archives of ophthalmology 125.1 (2007): 128-135.
Ito, Y. A., et al. "Severe molecular defects of a novel FOXC1 W152G mutation result in aniridia." Investigative ophthalmology & visual science 50.8 (2009): 3573-3579.
Kawase, C., et al. "Screening for mutations of Axenfeld-Rieger syndrome caused by FOXC1 gene in Japanese patients." Journal of glaucoma 10.6 (2001): 477-482.
Khan, A. O., et al. "Heterozygous FOXC1 mutation (M161K) associated with congenital glaucoma and aniridia in an infant and a milder phenotype in her mother." Ophthalmic genetics 29.2 (2008): 67-71.
Komatireddy, S., et al. "Mutation spectrum of FOXC1 and clinical genetic heterogeneity of Axenfeld-Rieger anomaly in India." Mol Vis 9 (2003): 43-48.
Koo, H-Y, et al. FoxC1-dependent regulation of VEGF signaling in corneal avascularity. Trends Cardiovasc Med. Jan. 2013; 23(1):1-4.
Kwon YS et al., "Inhibition of corneal neovascularization by rapamycin." Exp Mol Med. 2006;38(2):173-9.
Lai, L-J, et al. "Inhibition of corneal neovascularization with endostatin delivered by adeno-associated viral (AAV) vector in a mouse corneal injury model." Journal of biomedical science 14.3 (2007): 313-322.
Liu et al., "Gene-based antiangiogenic applications for corneal neovascularization,". Surv Ophthalmol. 2018;63(2):193-213.
Liu et al., "Recent drug therapies for corneal neovascularization." Chem Biol Drug Des. 2017;90(5):653-64.
Mears, A. J., et al. "Mutations of the forkhead/winged-helix gene, FKHL7, in patients with Axenfeld-Rieger anomaly." The American Journal of Human Genetics 63.5 (1998): 1316-1328.
Medina-Trillo, C., et al. "Hypo-and hypermorphic FOXC1 mutations in dominant glaucoma: transactivation and phenotypic variability." PLoS One 10.3 (2015): e0119272.
Micheal, S., et al. "A novel homozygous mutation in FOXC1 causes Axenfeld Rieger Syndrome with congenital glaucoma." PLoS one 11.7 (2016): e0160016.
Mirzayans F. et al., "Mutation of the PAX6 Gene in Patients with Autosomal Dominant Keratitis," Am. J. Hum. Genet. 57:539-548, 1995.

(56) References Cited

OTHER PUBLICATIONS

Morbidelli et al., "The Rabbit Corneal Pocket Assay." Methods Mol Biol. 2016;1430:299-310.

Murata et al., "Inhibitory effect of triamcinolone acetonide on corneal neovascularization." Graefes Arch Clin Exp Ophthalmol. 2006;244(2):205-9.

Murphy, T. C., et al. "The wing 2 region of the FOXC1 forkhead domain is necessary for normal DNA-binding and transactivation functions." Investigative ophthalmology & visual science 45.8 (2004): 2531-2538.

Narang, S. A., et al. "[6] Improved phosphotriester method for the synthesis of gene fragments." Methods in Enzymology. vol. 68. Academic Press, 1979. 90-98.

Nishimura, D. Y., et al. "A spectrum of FOXC1 mutations suggests gene dosage as a mechanism for developmental defects of the anterior chamber of the eye." The American Journal of Human Genetics 68.2 (2001): 364-372.

Nishimura, D. Y., et al. "The forkhead transcription factor gene FKHL7 is responsible for glaucoma phenotypes which map to 6p25." Nature genetics 19.2 (1998): 140-147.

Olferiev MA et al. "Use of Cell-Penetrating Peptide Technology for intracellular delivery of physiologically active peptides" Critical Technologies. Membranes, 2003 No. 17, pp. 30-35. With machine translation.

Owczarzy, R., et al. (2008). Predicting stability of DNA duplexes in solutions containing magnesium and monovalent cations. Biochemistry, 47(19), 5336-5353.

Panicker, S. G., et al. "Novel mutation in FOXC1 wing region causing Axenfeld-Rieger anomaly." Investigative ophthalmology & visual science 43.12 (2002): 3613-3616.

Prosser et al., "PAX6 mutations reviewed." Hum Mutat. 1998; 11(2):93-108.

Qazi et al., "Corneal transparency: genesis, maintenance and dysfunction." Brain Res Bull. 2010;81(2-3):198-210.

Ramaesh T, et al. Corneal abnormalities in Pax6+/- small eye mice mimic human aniridia-related keratopathy. Invest Ophthalmol Vis Sci. 2003;44(5):1871-8.

\* cited by examiner

OVEREXPRESSION OF FOXC1 TO TREAT CORNEAL VASCULARIZATION

CROSS-REFERENCE TO RELATED PATENT APPLICATIONS

The present application claims the benefit of priority under 35 U.S.C. § 119(e) to U.S. Provisional Application No. 62/637,795, filed on Mar. 2, 2018, the content of which is incorporated herein by reference in its entirety.

BACKGROUND

The field of the invention relates to methods for treating corneal vascularization. In particular, the field of the invention relates to methods, compounds, and compositions for treating and inhibiting corneal vascularization associated with bacterial or viral infection, chemical injury, autoimmune conditions, and post-corneal transplantation in subjects in need thereof, or in subjects having genetic mutations that predispose the subjects to corneal vascularization. The methods typically include administering treatment that results in overexpression of FOXC1.

The cornea is normally devoid of blood vessels, and corneal vascularization is a sight-threatening condition. Corneal transparency and avascularity are critical for proper ocular function and can be impaired by corneal neovascularization, which derives from the pathological growth of corneal vessels. (See, e.g., Qazi et al., "Corneal transparency: genesis, maintenance and dysfunction." Brain Res Bull. 2010; 81(2-3):198-210; the content of which is incorporated herein by reference in its entirety).

Corneal vascularization can occur due to a number of etiologies. For example, corneal vascularization also can occur in response to a wide range of insults, including bacterial or viral infections, trauma, chemical burns, and inflammation. (See, e.g., Regenfuss et al., "Conical (lymph) angiogenesis—from bedside to bench and back: a tribute to Judah Folkman Lymphat Res Biol. 2008; 6(3-4):191-201; the content of which is incorporated herein by reference in its entirety). In addition, genetic mutations in the PAX6 gene have been shown to be associated with autosomal dominant keratitis, which is characterized by vascularization and opacification of the cornea. (See, e.g., Mirzayans et al., "Mutation of the PAX6 Gene in Patients with Autosomal Dominant Keratitis," Am. J. Hum. Genet. 57:539-548, 1995, the content of which is incorporated herein by reference in its entirety).

Corneal vascularization also may result as a complication from corneal transplantation. More than 1.2 million Americans suffer from impaired corneas, and 40,000 people per year undergo corneal transplantation therapy to restore eyesight that has been compromised. (See, e.g., Liu et al., "Gene-based antiangiogenic applications for corneal neovascularization,". Surv Ophthalmol. 2018; 63(2):193-213; and Mohan et al., "Corneal gene therapy: basic science and translational perspective." The ocular surface. 2013; 11(3):150-64; the contents of which are incorporated herein by reference in their entireties). Corneal vasculization may develop in response to rejection of a corneal transplant.

Currently, no effectively treatments are available for corneal neovascularization. (See, e.g., Gupta et al., "Treatments for corneal neovascularization: a review." Cornea. 2011; 30(8):927-38; the content of which is incorporated herein by reference in its entirety). Therefore, there is an urgent need to develop new therapeutic strategies for improving vision in affected patients.

Mutations or changes in the copy number of human FOXC1 are associated with autosomal-dominant Axenfeld-Rieger syndrome (ARS), which is characterized by anterior eye segment defects, glaucoma and corneal neovascularization. (See, e.g., Alward, W. L. "Axenfeld-Rieger syndrome in the age of molecular genetics." Am J Ophthalmol. 2000; 130(1):107-15; Chang et al. "Axenfeld-Rieger syndrome: new perspectives." Br J Ophthalmol. 2012; 96(3):318-22; and Tumer et al., Axenfeld-Rieger syndrome and spectrum of PITX2 and FOXC1 mutations." Eur J Hum Genet. 2009; 17(12):1527-39; the contents of which are incorporated herein by reference in their entireties. The present inventors have recently shown that deletion of Foxc1 in mice recapitulates anterior-segment defects including corneal neovascularization observed in patients with ARS secondary to heterozygous FOXC1 mutations. (See Seo et al., "Forkhead box transcription factor FoxC1 preserves corneal transparency by regulating vascular growth." Proc Natl Acad Sci USA. 2012; 109(6):2015-20; the content of which is incorporated herein by reference in its entirety). This observation indicates that FOXC1 plays a key role in keeping the cornea devoid of vascularization.

Here, the inventors show that FOXC1 can be expressed or overexpressed in the cornea in order to inhibit corneal vascularization. In particular, the inventors show that overexpression of FOXC1 by adeno-associated virus (AAV) in adult mice suppresses corneal neovascularization by alkali-burn injury. Corneal vascularization developing from alkali-burn injury is recognized as a model for corneal vascularization in general. (See Anderson, et al., "An alkali-burn injury model of corneal neovascularization in the mouse. J Vis Exp. 2014(86); the content of which is incorporated herein by reference in its entirety). As such, the inventor's results indicate that the overexpression of FOXC1 can be used to inhibit corneal vascularization that derives from different etiologies such as infection, trauma, and graft rejection following corneal transplant.

SUMMARY

Disclosed are methods and pharmaceutical compositions for treating and inhibiting corneal vascularization including corneal vascularization associated with viral infection, chemical injury, autoimmune conditions, and post-corneal transplantation or in subjects having a PAX6 mutation associated with corneal vascularization. The methods and pharmaceutical compositions are utilized in administering treatment that results in increased concentration of FOXC1 in a subject's cornea in order to treat or inhibit corneal vascularization.

DETAILED DESCRIPTION

Definitions

Figure 1A:
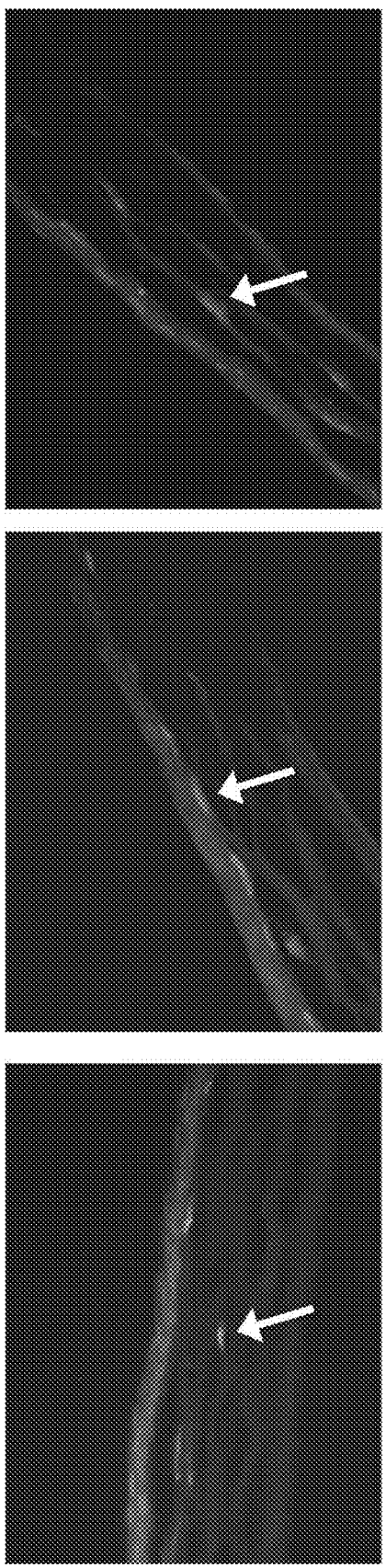
FIG. 1A. Mice cornea were infected with adenovirus-associated virus 8 (AAV8) vector CMV-EGFP which expresses enhanced green fluorescent protein (EGFP), and expression of EGFP was visualized.

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a therapeutic agent" should be interpreted to mean "one or more therapeutic agents." As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "modulate" means decreasing or inhibiting and/or increasing or augmenting. For example, modulating FOXC1 expression may mean increasing or augmenting FOXC1 expression and/or decreasing or inhibiting FOXC1 expression. Modulating FOXC1 biological activity may mean increasing or augmenting FOXC1 biological activity and/or decreasing or inhibiting FOXC1 biological activity. The therapeutic agents disclosed herein may be administered to a subject in need thereof to modulate FOXC1 expression and/or FOXC1 biological activity.

FOXC1

As used herein, the term "FOXC1" refers to the human protein encoded by the KALRN gene, or non-human equivalents thereof. FOXC1 may also be referred to as "forkhead box protein C1." FOXC1 is a DNA-binding transcription factor that is important in a number of developmental processes including the development of the eye. (See Berry et al., J. Biol. Chem. 277:10292-10297 (2002); Saleem et al., Nucl. Acids Res. 32:4182-4193(2004); Berry et al., Mol. Ce. Biol. 25:1415-1424 (2005); Berry et al., J. Biol. Chem. 281:10098-10104 (2006); Bin et al., PLoS ONE 11:E0167392-E0167392 (2016); Saleem et al., Hum. Mol. Genet. 12:2993-3005 (2003); Saleem et al., Invest. Ophthalmol. Vis. Sci. 44:4608-4612 (2003); Murphy et al., Invest. Ophthalmol. Vis. Sci. 45:2531-2538 (2004); Berry et al., Hum. Genet. 15:905-919 (2006); Ito et al., Arch. Ophthalmol. 125:128-135 (2007); Fetterman et al., Clin. Genet. 76:296-299 (2009); Ito et al., Invest. Ophthalmol. Vis. Sci. 50:3573-3579 (2009); Meina-Trillo et al., PLoS ONE 10:E0119272-E0119272 (2015); and Seifi et al., Hum. Mutat. 38:169-179 (2017); the contents of which are incorporated herein by reference in their entireties. The amino acid sequence of human FOXC1 is provided herein as SEQ ID NO:1. Variants of FOXC1 are contemplated herein as discussed below.

Subject in Need Thereof

As used herein, a "subject" may be interchangeable with "patient" or "individual" and means an animal, which may be a human or non-human animal, in need of treatment.

As used herein, the term "a subject in need thereof" refers to a human or non-human subject that can be treated with any of the therapeutic agents disclosed herein. A subject in need thereof may include a subject having or at risk for developing corneal vascularization. In some embodiments, a subject having or at risk for developing corneal vascularization may include a subject having or at risk for developing corneal vascularization further to a bacterial infection or viral infection, a subject having or at risk for developing corneal vascularization further to trauma such as chemical injury or physical injury to the cornea, a subject having or at risk for developing corneal vascularization further to an autoimmune reaction, and/or a subject having or at risk for developing corneal vascularization further to a complication after a corneal transplant such as corneal rejection after corneal transplant. A subject having or at risk for developing corneal vascularization may include a subject having a genetic mutation that results in corneal vascularization such as, but not limited to, one or more mutations in the PAX6 gene. (See, e.g., Prosser et al., "PAX6 mutations reviewed." Hum Mutat. 1998; 11(2):93-108; and Mirzayans et al., "Mutation of the PAX6 Gene in Patients with Autosomal Dominant Keratitis." Am. J. Hum. Genet. 57:539-548, 1995; the contents of which are incorporated by reference in their entireties). Mutations in PAX6 are associated with anterior segment dysgenesis and keratitis hereditary. A subject in need thereof may include a subject having or at risk for developing anterior segment dysgenesis (e.g., anterior segment dysgenesis 5) and/or keratitis hereditary. The amino acid sequence of human PAX6 is provided herein as SEQ ID NO:2, which is encoded by the PAX6 gene.

Therapeutic Agents

As used herein, a therapeutic agent may refer to any agent that is administering to a subject in thereof in order to treat the subject. A therapeutic agent may refer to an agent that modulates expression and/or concentration of FOXC1 in the cornea, for example, an agent that increases expression and/or concentration of FOXC1 in the cornea. A therapeutic agent may refer to an agent that modulates a biological activity of FOXC1 in the cornea, for example where the agent increases biological activity of FOXC1 in the cornea. Therapeutic agents may include, but are not limited to, small molecules or compounds, peptides, proteins (e.g., peptides or proteins comprising at least a fragment of the amino acid sequence of FOXC1 (e.g., SEQ ID NO:1), and nucleic acids (e.g., nucleic acids encoding a peptide or protein comprising at least a fragment of the amino acid sequence of FOXC1 (e.g., SEQ ID NO:1)). Therapeutic agents may include, but are not limited to, pharmaceutical compositions comprising small molecules, compounds, peptides, proteins, and/or vectors that express FOXC1 or a variant thereof.

Polynucleotides and Synthesis Methods

Polynucleotides and uses thereof may be disclosed herein such as polynucleotides encoding at least a fragment of the amino acid sequence of FOXC1 (e.g., a polynucleotide encoding SEQ ID NO:1) or a variant thereof. The terms "polynucleotide (or "nucleic acid" and "oligonucleotide") refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

A "fragment" of a polynucleotide is a portion of a polynucleotide sequence which is identical in sequence to but shorter in length than a reference sequence. As used herein, a reference sequence may include a polynucleotide sequence encoding FOXC1 (e.g., a polynucleotide sequence encoding SEQ ID NO:1) or a variant thereof. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full length polynucleotide. A "variant," "mutant," or "derivative" of a reference polynucleotide sequence may include a fragment of the reference polynucleotide sequence.

Regarding polynucleotide sequences and variants thereof, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

The term "promoter" as used herein refers to a cis-acting DNA sequence that directs RNA polymerase and other trans-acting transcription factors to initiate RNA transcription from the DNA template that includes the cis-acting DNA sequence.

As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides. As used herein, the term "complementary" may refer to the ability of a first polynucleotide to hybridize with a second polynucleotide due to base-pair interactions between the nucleotide pairs of the first polynucleotide and the second polynucleotide (e.g., A:T, A:U, C:G, G:C, G:U, T:A, U:A, and U:G).

As used herein, the term "complementarity" may refer to a sequence region on an anti-sense strand that is substantially complementary to a target sequence but not fully complementary to a target sequence. Where the anti-sense strand is not fully complementary to the target sequence, mismatches may be optionally present in the terminal regions of the anti-sense strand or elsewhere in the anti-sense strand. If mismatches are present, optionally the mismatches may be present in terminal region or regions of the anti-sense strand (e.g., within 6, 5, 4, 3, or 2 nucleotides of the 5' and/or 3' terminus of the anti-sense strand).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions." Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

The term "promoter" refers to a cis-acting DNA sequence that directs RNA polymerase and other trans-acting transcription factors to initiate RNA transcription from the DNA template that includes the cis-acting DNA sequence.

In certain exemplary embodiments, vectors such as, for example, expression vectors, containing a nucleic acid encoding one or more polypeptides and/or proteins described herein are provided (e.g., vectors encoding and/or expressing FOXC1). As used herein, the term "vector" refers to a nucleic acid molecule capable of transporting and/or expressing another nucleic acid to which it has been linked. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

As used herein, a "viral vector" (e.g., an adenovirus or adeno-associated virus, Sendai virus, or measles virus vector) refers to recombinant viral nucleic acid that has been engineered to express a heterologous polypeptide (e.g., FOXC1 or a variant thereof). The recombinant viral nucleic acid typically includes cis-acting elements for expression of the heterologous polypeptide. The recombinant viral nucleic acid typically is capable of being packaged into a helper virus that is capable of infecting a host cell. For example, the recombinant viral nucleic acid may include cis-acting elements for packaging. Typically, the viral vector is not replication competent or is attenuated. An "attenuated recombinant virus" refers to a virus that has been genetically altered by modern molecular biological methods (e.g., restriction endonuclease and ligase treatment, and rendered less virulent than wild type), typically by deletion of specific genes. For example, the recombinant viral nucleic acid may lack a gene essential for the efficient production or essential for the production of infectious virus. The recombinant viral nucleic acid, packaged in a virus (e.g., a helper virus) may be introduced into a human subject by standard methods.

Numerous virus species can be used as the recombinant virus vectors for the pharmaceutical composition disclosed herein. A preferred recombinant virus is adeno-associated virus. Others include adenoviruses, retroviruses that are packaged in cells with amphotropic host range, vaccinia virus, canarypox, Sendai virus, measles virus, Yellow Fever vaccine virus (e.g., 17-D or similar), attenuated or defective DNA viruses, such as but not limited to herpes simplex virus (HSV), papillomavirus, and Epstein Barr virus (EBV).

In certain exemplary embodiments, the recombinant expression vectors comprise a nucleic acid sequence in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Peptides, Polypeptides, Proteins, and Synthesis Methods

Peptides, polypeptides, and proteins and uses thereof may be disclosed herein such as peptides, polypeptides, and proteins comprising at least a fragment of the amino acid sequence of FOXC1 (SEQ ID NO:1) or a variant thereof. As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine). Modifications may include the addition of a glycosylation tag (e.g., 4×DQNAT optionally at the C-terminus) and/or a histidine tag (e.g., 6×His).

Reference may be made herein to peptides, polypeptides, proteins and variants thereof. Reference amino acid sequences may include, but are not limited to, an amino acid sequence comprising at least a fragment of the amino acid sequence of FOXC1 (e.g., SEQ ID NO:1) or a variant thereof. Variants as contemplated herein may have an amino acid sequence that includes conservative amino acid substitutions relative to a reference amino acid sequence (e.g., relative to the amino acid sequence of SEQ ID NO:1). For example, a variant peptide, polypeptide, or protein as contemplated herein may include conservative amino acid substitutions and/or non-conservative amino acid substitutions relative to a reference peptide, polypeptide, or protein. "Conservative amino acid substitutions" are those substitutions that are predicted to interfere least with the properties of the reference peptide, polypeptide, or protein, and "non-conservative amino acid substitution" are those substitution that are predicted to interfere most with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

TABLE 1

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally disrupt: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain.

Variants comprising deletions relative to a reference amino acid sequence of peptide, polypeptide, or protein are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Variants comprising fragment of a reference amino acid sequence of a peptide, polypeptide, or protein are contemplated herein. A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide.

Variants comprising insertions or additions relative to a reference amino acid sequence of a peptide, polypeptide, or protein are contemplated herein. The words "insertion" and "addition" refer to changes in an amino acid or sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues.

Fusion proteins also are contemplated herein. A "fusion protein" refers to a protein formed by the fusion of at least one peptide, polypeptide, or protein or variant thereof as disclosed herein to at least one heterologous protein peptide, polypeptide, or protein (or fragment or variant thereof). The heterologous protein(s) may be fused at the N-terminus, the C-terminus, or both termini of the peptides or variants thereof.

Particularly disclosed herein are fusion proteins comprising FOXC1 or a variant thereof fused to one or more cell penetrating peptides as known in the art. (See, e.g., Derakhshankhah et al., Biomedicine & Pharmacotherapy 108 (2018) 1090-1096; the content of which is incorporated by reference in its entirety). The fusion proteins contemplated herein comprising FOXC1 or a variant thereof fused to one or more cell penetrating peptides may include FOXC1 having one or more cell penetrating peptides fused at the N-terminus, the C-terminus, or both termini.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number (e.g., any of SEQ ID NOs:1-10), or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide (e.g., glycosylase activity or other activity). "Substantially isolated or purified" amino acid sequences are contemplated herein. The term "substantially isolated or purified" refers to amino acid sequences that are removed from their natural environment, and are at least 60% free, preferably at least 75% free, and more preferably at least 90% free, even more preferably at least 95% free from other components with which they are naturally associated. Variant polypeptides as contemplated herein may include variant polypeptides of any of SEQ ID NOs:1-10).

Pharmaceutical Formulation

The disclosed therapeutic agents may be formulated as pharmaceutical compositions for administering to a subject in need thereof. The disclosed pharmaceutical compositions may include: (a) a therapeutic agent as discussed herein (e.g., an effective amount of a therapeutic agent for treating a disease or disorder associated with corneal vascularization); and (b) one or more pharmaceutically acceptable carriers, excipients, or diluents.

The therapeutic agents utilized in the methods disclosed herein may be formulated as a pharmaceutical composition that includes one or more carrier agents, binding agents, filling agents, lubricating agents, suspending agents, buffers, wetting agents, and/or preservatives. Examples of preservatives may include potassium sorbate, methylparaben, propylparaben, benzoic acid and its salts, other esters of para-hydroxybenzoic acid such as butylparaben, alcohols such as ethyl or benzyl alcohol, phenolic compounds such as phenol, or quaternary compounds such as benzalkonium chloride.

The therapeutic agents utilized in the methods disclosed herein may be formulated as a pharmaceutical composition for delivery via any suitable route. For example, the pharmaceutical composition may be administered topically to the surface of a cornea.

The therapeutic agents utilized in the methods disclosed herein may be administered in conventional dosage forms prepared by combining the active ingredient with standard pharmaceutical carriers or diluents according to conventional procedures well known in the art. These procedures may involve mixing or dissolving the ingredients as appropriate to the desired preparation.

Pharmaceutical compositions comprising the therapeutic agents may be adapted for administration by any appropriate route, for example topically to the surface of the cornea. Such formulations may be prepared by any method known in the art of pharmacy, for example by bringing into association the active ingredient with the carrier(s) or excipient(s).

Illustrative Embodiments

The following embodiments are illustrative and should not be interpreted to limit the scope of the claimed subject matter.

Embodiment 1

A method for treating and/or inhibiting corneal vascularization in a subject in need thereof, the method comprising administering a therapeutic agent to the subject that results in an increase in concentration of FOXC1 in the cornea of the subject than the concentration of FOXC1 in the cornea of the subject prior to administering the therapeutic agent.

Embodiment 2

The method of embodiment 1, wherein the therapeutic agent is administered to the cornea of the subject, for example, wherein the therapeutic agent is administered to the surface of the cornea of the subject.

Embodiment 3

The method of embodiment 1 or 2, wherein the therapeutic agent is a vector that expresses FOXC1 or a variant thereof comprising an amino acid sequence having at least about 80% sequence identity to SEQ ID NO:1.

Embodiment 4

The method of any of embodiments 1-3, wherein the therapeutic agent is a viral vector that expresses FOXC1 or a variant thereof comprising an amino acid sequence having at least about 80% sequence identity to SEQ ID NO:1.

Embodiment 5

The method of any of embodiments 1-4, wherein the therapeutic agent is an adenovirus-associated viral vector that expresses FOXC1 or a variant thereof comprising an amino acid sequence having at least about 80% sequence identity to SEQ ID NO:1.

Embodiment 6

The method of any of the foregoing embodiments, wherein the subject has or at risk for developing corneal vascularization from bacterial or viral infection.

Embodiment 7

The method of any of the foregoing embodiments, wherein the subject has or is at risk for developing corneal vascularization from chemical injury.

Embodiment 8

The method of any of the foregoing embodiments, wherein the subject has or is at risk for developing corneal vascularization from an autoimmune response.

Embodiment 9

The method of any of the foregoing embodiments, wherein the subject has or is at risk for developing corneal vascularization after a corneal transplant.

Embodiment 10

The method of any of the foregoing embodiments, wherein the subject has a PAX6 mutation and the subject has or is at risk for developing corneal vascularization due to the PAX6 mutation.

Embodiment 11

A vector that is capable of expressing FOXC1 in a cornea of a subject in need thereof.

Embodiment 12

The vector of embodiment 11, wherein the vector is capable of expressing FOXC1 or a variant thereof comprising an amino acid sequence having at least about 80% sequence identity to SEQ ID NO:1 in the cornea of the subject in need thereof.

Embodiment 13

The vector of embodiment 11 or 12, wherein the vector is a viral vector.

Embodiment 14

The vector of embodiment 11 or 12, wherein the vector is a adenovirus-associated viral vector.

Embodiment 15

A pharmaceutical composition comprising: (i) FOXC1 or a variant thereof comprising an amino acid sequence having at least about 80% sequence identity to SEQ ID NO:1; and (ii) a carrier, excipient, or diluent.

Embodiment 16

A pharmaceutical composition comprising: (i) FOXC1 or a variant thereof comprising an amino acid sequence having at least about 80% sequence identity to SEQ ID NO:1 fused to one or more cell penetrating peptides; and (ii) a carrier, excipient, or diluent.

Embodiment 17

A method for identifying a test subject having or at risk for developing corneal vascularization, the method comprising: (i) detecting expression levels of FOXC1 in a cornea of the test subject; (ii) comparing the detecting expression levels of FOXC1 in the cornea of the test subject to expression levels of FOXC1 in a cornea of a control subject not having or at risk for developing corneal vascularization; and (iii) determining that the test subject has lower expression levels of FOXC1 in the cornea compared to expression levels of FOXC1 in the cornea of the control subject.

Embodiment 18

The method of embodiment 17, further comprising administering a therapeutic agent to the test subject that results in an increased in concentration of FOXC1 in the cornea of the test subject relative to the concentration of FOXC1 in the cornea of the test subject prior to administering the therapeutic agent.

Embodiment 19

The method of embodiment 18, wherein the therapeutic agent is administered to the cornea of the subject.

Embodiment 20

The method of embodiment 18, wherein the therapeutic agent is a vector that expresses FOXC1 or a variant thereof comprising an amino acid sequence having at least about 80% sequence identity to SEQ ID NO:1.

Embodiment 21

The method embodiment 18, wherein the therapeutic agent is a viral vector that expresses FOXC1 or a variant thereof comprising an amino acid sequence having at least about 80% sequence identity to SEQ ID NO:1.

Embodiment 22

The method of embodiment 18, wherein the therapeutic agent is an adenovirus-associated viral vector that expresses FOXC1 or a variant thereof comprising an amino acid sequence having at least about 80% sequence identity to SEQ ID NO:1.

EXAMPLES

The following examples are illustrative and should be interpreted to limit the scope of the claimed subject matter.

Example 1—Inhibition of Traumatic Model of Corneal Vascularization with Overexpression of FOXC1

Background

Mutations or changes in the copy number of human FOXC1 are associated with autosomal-dominant Axenfeld-Rieger syndrome (ARS), which is characterized by anterior eye segment defects, glaucoma and corneal neovascularization. Our group have recently shown that murine Foxc1 is expressed in neural crest (NC)-derived periocular mesenchymal cells and that NC-specific deletion of Foxc1 in mice recapitulates anterior-segment defects (including corneal neovascularization) observed in patients with ARS secondary to heterozygous FOXC1 mutations. Here we show that overexpression of FOXC1 by adeno-associated virus (AAV) in adult mice suppresses corneal neovascularization either by alkali-burn injury or in Pax6 heterozygous mutant mice that develop corneal neovascularization in a similar manner to patients with heterozygous PAX6 mutation.

Methods

Figure 1B:
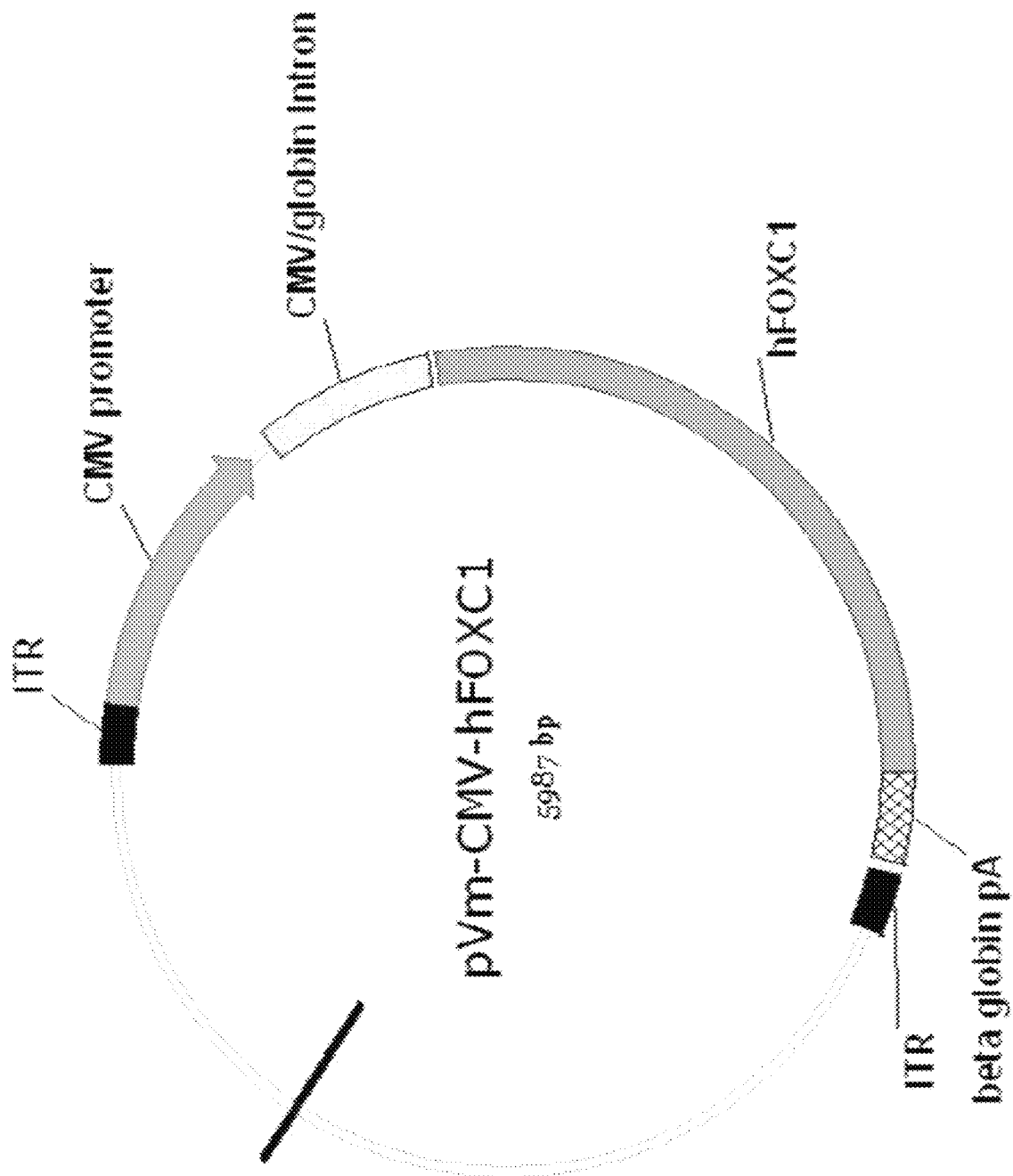
FIG. 1B. Schematic of adenovirus-associated virus 8 (AAV8) vector for expressing human FOXC1 (hFOXC1).

To overexpress FOXC1 in the mouse cornea, AAV8-FOXC1 and AAV8-GFP (control) were generated (FIG. 1A and FIG. 1B). To test the effects of AAV8-FOXC1 on corneal neovascularization, we employed an alkali-burn injury model. (See, e.g., Seo et al. PNAS 109: 2015-2020, 2012; the content of which is incorporated herein by reference in its entirety).

Fifteen (15) mice (C57BL6) were obtained at age 8 weeks. The respective AAV vector was delivered to both mouse corneas by using drop delivery method, and ten (10) days later alkaline burn injury was performed on one eye of the mice.

Drop delivery of AAV-FoxC1 and AAV-GFP were performed as follows. Mice were anaesthetized with intraperitoneal injection of ketamine (100 mg/kg) and xylazine (9 mg/kg). Topical solution of 1% proparacaine hydrochloride (Alcon, Ft. Worth, Tex.) were instilled to each eye for local anesthesia. 100% ethanol soaked gauze were applied on each cornea for 20-30 seconds and epithelium were removed by gentle scraping with a #64 Beaver blade (Becton-Dickinson, Franklin Lakes, N.J.) under an operating microscope. After flushing the eye with sterile saline and drying the cornea with merocel sponge, two microliters of viral vector (viral titer 249 genomic copies/µl) applied to the corneal stroma for 2 minutes. FoxC1-AAV vector was delivered to 7 mice, and GFP-AAV was delivered to 8 mice as control group. Eyes were again flushed with sterile saline and blotted dry prior to application of erythromycin ophthalmic ointment to prevent infection. The meloxicam was administered for 3 days on all surgery mice for pain management purpose.

Animals were allowed to recover from surgery for ten (10) days. After 10 days corneal alkaline burn injury surgery was performed on the mice. The mice were anesthetized by intra-peritoneal injection of Ketamine (90 mg/kg) and Xylazine (9 mg/kg). Following anesthesia, the right eye of the mouse received a drop of proparacaine ophthalmic solution (topical anesthesia) for a minute. Adequate depth of anesthesia was assessed by lack of response to toe pinch. Body temperature was maintained throughout the procedures by placing animals on water circulating pads or other appropriate heating pad covered with sterile drape. The surgical field was maintained at all times through the use of aseptic technique. Sterile forceps was used and a hot bead sterilizer was used to maintain sterility of all instruments used. Two packs of sterile instruments was used and alternated with hot bead sterilization between individual animals. For Corneal Alkaline Injury, Whatmann #3 filter paper of 2 mm diameter (cut using a 2 mm trephine) soaked in 2 uL of 1N NaOH solution was then placed on the center of the anesthetized right eye for one minute. Following administration of the NaOH solution, the eye was extensively washed using normal saline (5-10 ml). After surgery, a drop of proparacaine ophthalmic solution was applied to the right eye once daily to minimize the pain for 3 days, followed by topical antibiotic (Erythromycin Opthalmic Ointment) application to the injured eye once daily for 3 days to minimize any possible risk of corneal infection. The meloxicam was administered for 3 days for pain management purpose.

Results

Figure 2A:
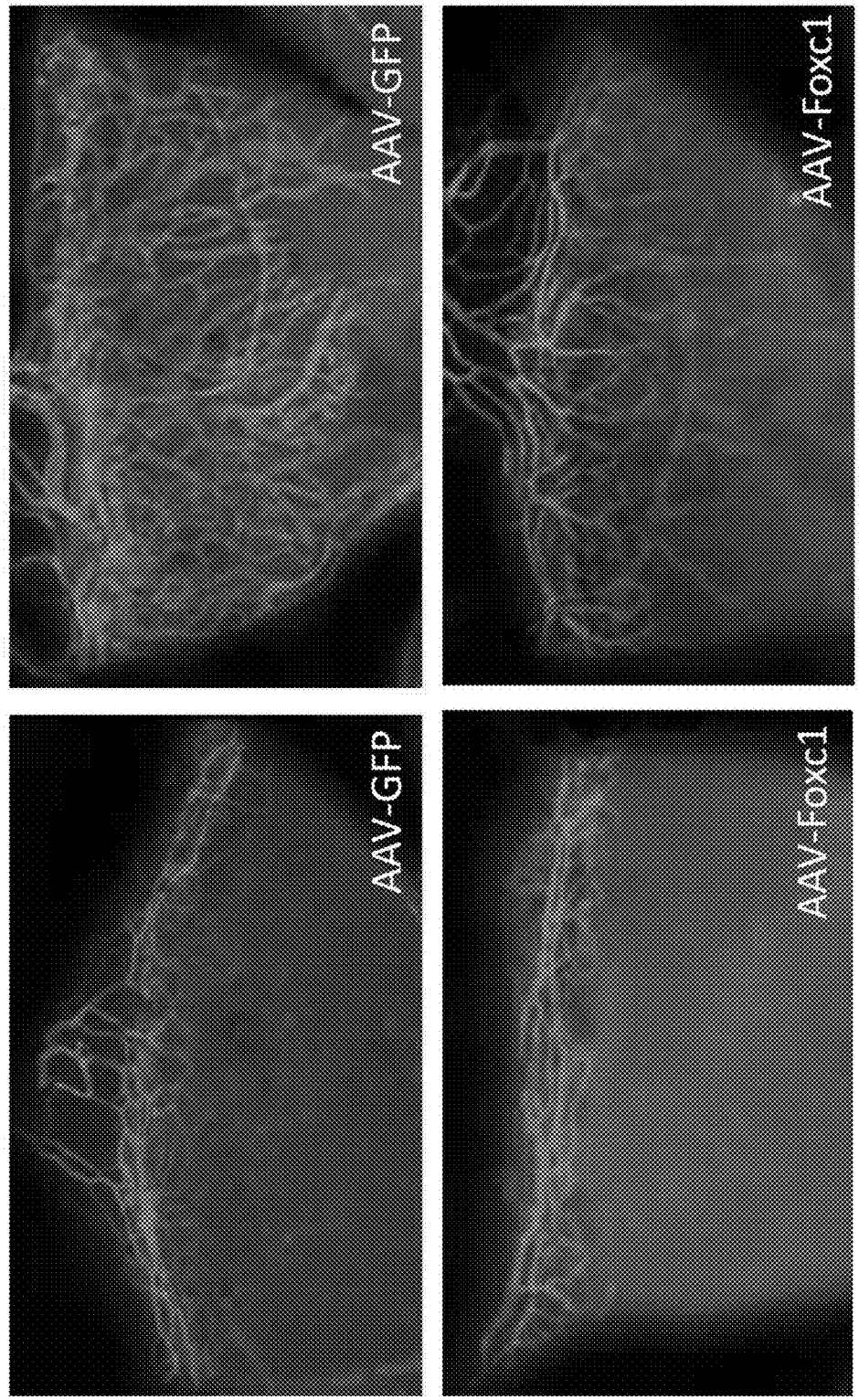
FIG. 2A. AAV-FOXC1 infection significantly inhibited alkali burn induced corneal angiogenesis in wild type mice. Eight mice were treated with AAV-GFP, and 7 mice were treated with AAV-FOXC1.
Figure 2B:
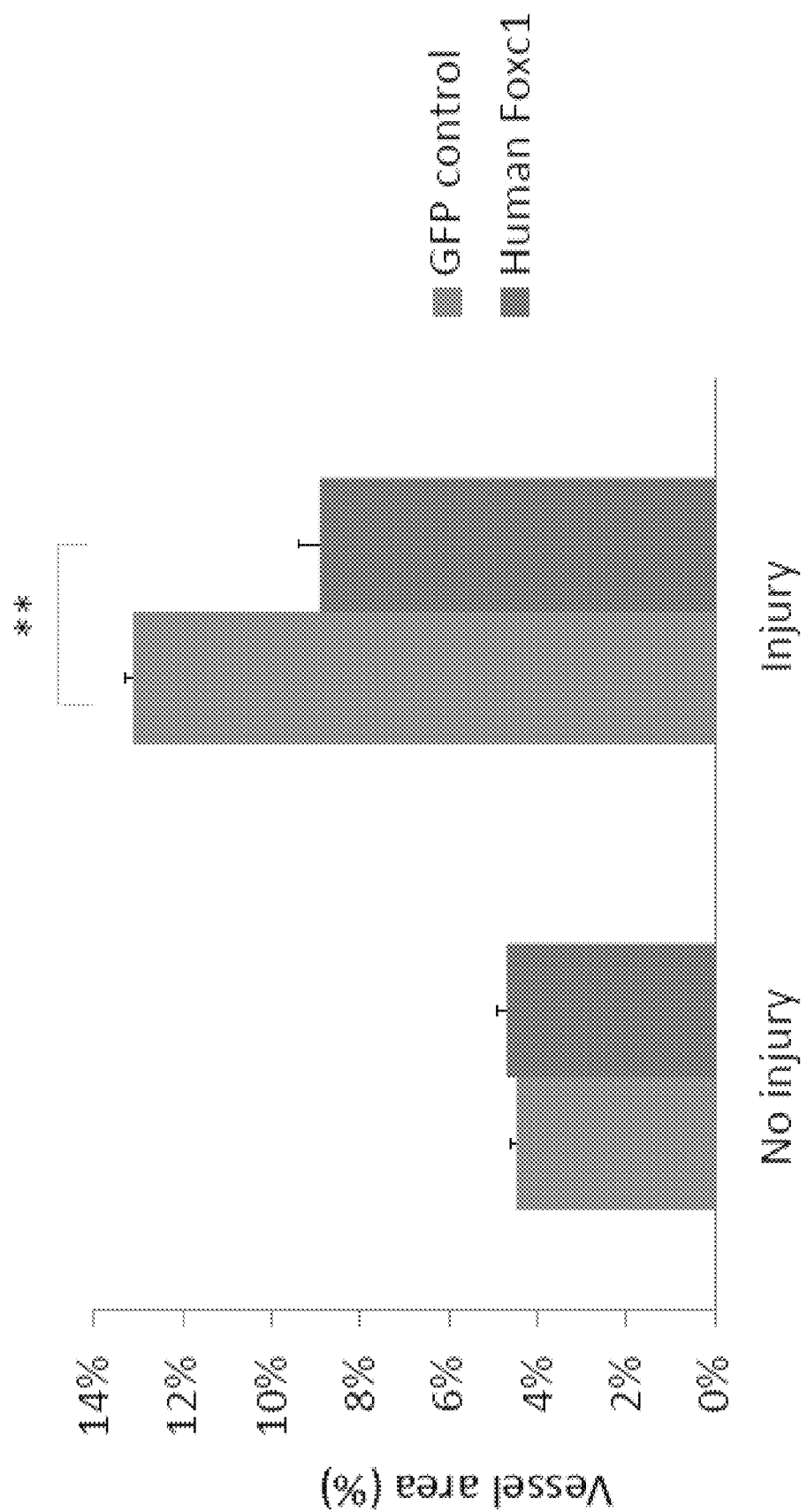
FIG. 2B. Graphical representation of results from experiments described in FIG. 2A.

In the alkali burn injury model, AAV8-mediated delivery of FOXC1 ameliorated pathologically-induced corneal angiogenesis in adult wild-type mice compared to control corneas with AAV8-GFP BY ~25% (FIG. 2A and FIG. 2B). All the results represented statistically significant reductions, and the experiment was performed with 3 different combinations of murine age and or time interval between treatment application and assessment of degree of neovascularization.

Discussion

Our data suggest that overexpression of FOXC1 inhibits corneal neovascularizatrion in alkaline-burn corneal injury. Further analysis is under way to determine whether FOXC1 overexpression can also rescue other corneal abnormalities such as corneal conjunctivalization.

Applications of the disclosed subject matter include, but are not limited to, (i) adenovirus-associated viral vector delivery of FOXC1 to treat and/or inhibit corneal vascularization; and (ii) delivery FOXC1 protein in eyedrops using cell-penetrating peptides, liposomes, or analogous approaches. Advantages of the disclosed subject matter include, but are not limited to, (i) treatment of causes of corneal vascularization such as infective causes, traumatic causes, and causes derived from complications following corneal transplantation; and (ii) treatment of corneal vascularization developing in subjects having PAX6 mutations that are characterized by corneal vascularization.

Corneal avascularity is essential for proper ocular surface function and can be impaired by corneal neovascularization, which is a vision-threatening condition and can occur in response to a wide range of insults, including infections, trauma, chemical burns, and inflammation, as well as during recovery from corneal transplantation surgery. Management of this condition has been hampered by a lack of effective therapeutic strategies. Our AAV-mediated gene therapy to express the FOXC1 gene will be a new therapeutic approach to treat corneal neovascularization.

Corneal neovascularization is typically caused by inflammatory responses such as traumatic injury, bacterial and viral infection, or chemical burns. In addition, corneal neovascularization often occurs in patients with corneal grafts often contributes to graft rejection. Patients with limbal stem cell deficiency, characterized by a loss of stem cells in the limbus of the eye that are essential for regeneration of corneal epithelium, are also involved. Mutations in PAX6 in humans lead to limbal stem cell deficiency, aniridia, and corneal neovascularization.

There are currently no effective treatments for corneal neovascularization. Available treatment options such as topical application of steroids or vascular endothelial growth factor (VEGF) inhibitors as well as surgical interventions are limited by insufficient efficacy, serious adverse effects, and short-term effectiveness. Corneal neovascularization is also a risk factor for graft rejection of corneal transplantation after keratoplasty. Patients with PAX6 mutation progressively lose their vision over 2-3 decades, and this is currently untreatable. Therefore, a gene-based therapy would be an alternative strategy to treat conical neovascularization. Since this corneal disease can be caused by traumas, infection, inflammation, chemical exposure, gene mutation, and conical graft, our AAV-mediated FOXC1 expression would be broadly used as a new therapeutic agent with high marketability.

Topical inhibition of vascular endothelial growth factor (VEGF) signaling using specific inhibitors such as ranibizumab and bevacizumab has been tested in patients to treat conical neovascularization. However, the effects of there treatments are transient and incomplete. (See, e.g., Feizi et al., "Therapeutic approaches for conical neovascularization." Eye Vis (Lond). 2017; 4:28; and Liu et al., "Recent drug therapies for conical neovascularization." Chem Biol Drug Des. 2017; 90(5):653-64; the contents of which are incorporated herein by reference in their entireties). Because anti-VEGF drugs also inhibit the physiological function of VEGF, raising a concern about potential side effects. (See id.). Therefore, more effective strategies need to be developed to treat corneal neovascularization. AAV-mediated gene therapy is an emerging and effective technology for corneal disease. AAV is nonpathogenic to humans so that it is a safe and attractive approach for gene delivery. Since AAV is known to establish sustained gene expression, it is also advantageous to long-lasting treatment effects. This approach may be of benefit in treating various causes of conical neovascularization (infective, traumatic, following corneal graft rejection) although such possibilities remain to be evaluated in animal models. Equally, there may be scope to apply such treatment to other vascular disorders in the eye, or elsewhere in the body. Potentially, the same approach that has yielded very promising results in Pax6 murine mutants can be applied to patients with a corresponding mutation.

In order to demonstrate whether the gene therapy using AAV-mediated expression of FOXC1 is applicable beyond our pathological mouse model to other causes of conical neovascularization, in future work we will employ a rabbit corneal neovascularization stimulated by basic fibroblast growth factor (bFGF) to test the efficacy and safety of AAV-mediated FOXC1 treatment. (See Morbidelli et al., "The Rabbit Corneal Pocket Assay." Methods Mol Biol. 2016; 1430:299-310; Kwon et al., "Inhibition of corneal neovascularization by rapamycin." Exp Mol Med. 2006; 38(2):173-9; and Murat et al., "Inhibitory effect of triamcinolone acetonide on conical neovascularization." Graefes Arch Clin Exp Ophthalmol. 2006; 244(2):205-9; the contents of which are incorporated herein by reference in their entireties). The proposed studies entail 3 doses of AAV-FOXC1 that bracket the dose intended for use in patients. It is important to generate preclinical data from a rabbit eye of relatively similar size to human, which is essential for dose calculations. A positive result with applicability will significantly enhance prospects for funding a clinical trial.

In the rabbit model of corneal neovascularization stimulated by bFGF pellets, New Zealand White rabbits (1.8-2.5 kg) will be systematically anesthetised, and the cornea surface will be locally anesthetised. Only one eye of each animal was used for conical neovascularization, whereas the other eye will be served as a negative control. An incision will be made in the mid-cornea, and a pocket perpendicular to the incision will be created in the corneal stroma using standard surgical tools. A sucralfate-hydron pellet containing bFGF (250 ng) will then be inserted into this pocket. To prevent infection, antibiotic ointment will be applied to the surface of the cornea. The rabbits will be divided into four groups. AAV8-GFP (viral titer $2.4 \times 10^9$ genomic copies/µl) or three different doses of AAV8-FOXC1 in 100 µl will be topically applied to the corneal stroma after gently removing the corneal epithelium by a surgical blade. To monitor and quantify the extent of AAV8-FOXC1 mediated inhibition of corneal neovascularization, the eyes will be imaged using a slit lamp with a digital camera at days 5, 10, 14 following bFGF pellet implantation.

To test the efficacy and potency of AAV8-FOXC1 transduction in the rabbit cornea, expression levels of exogenous human FOXC1 and GFP (control) will be quantified by qPCR using RNA isolated from the corneal tissues at days 5, 10, and 14 following bFGF pellet implantation and AAV infection. Because the AAV genome mainly stays as an episomal form in the nucleus of the infected cells (see Colella et al., "Emerging Issues in AAV-Mediated In Vivo Gene Therapy." Mol Ther Methods Clin Dev. 2018; 8:87-104, the content of which is incorporated herein by reference in its entirety), we will isolate genomic DNA from corneas infected with AAV8-FOXC1 and analyze the copy number of the exogenous human FOXC1 gene by qPCR. While it is a rare event, the integration of an AAV vector DNA into the infected cell may cause genotoxic effects. (See id.). Thus, we will examine whether the AAV8-FOXC1 vector is integrated into genomic DNA of the infected conical tissue by Southern blotting. If this is the case, we will identify integration sites in the host DNA.

To test if the dose planed for use in patients is safe, we will examine whether corneas infected with AAV8-FOXC1 (3 doses) does not opacify/disintegrate. Toxicity testing on the target organ (cornea and eye) will then be performed. Furthermore, a full biodistribution survey of other organs, including the brain, will also be carried out to test whether AAV-FOXC1 could be spread into the whole body from the eye.

Despite the immune-privileged nature of the cornea, it is possible that the human FOXC1 transgene used for this study may be immunogenic in rabbits. Therefore, we will assess the immunogenicity of AAV8-FOXC1 in the rabbit cornea by examining Innate immune responses such as T cell responses.

REFERENCES

1. Liu S, Romano V, Steger B, Kaye S B, Hamill K J, Willoughby C E. Gene-based antiangiogenic applications for corneal neovascularization. Surv Ophthalmol. 2018; 63(2):193-213. PMID: 29080632
2. Mohan R R, Rodier J T, Sharma A. Conical gene therapy: basic science and translational perspective. The ocular surface. 2013; 11(3):150-64. PMID: 23838017, PMCID: PMC3708266
3. Gupta D, Illingworth C. Treatments for corneal neovascularization: a review. Cornea. 2011; 30(8):927-38. PMID: 21389854
4. Qazi Y, Wong G, Monson B, Stringham J, Ambati B K. Conical transparency: genesis, maintenance and dysfunction. Brain Res Bull. 2010; 81(2-3):198-210. PMID: 19481138, PMCID:PMC3077112
5. Regenfuss B, Bock F, Parthasarathy A, Cursiefen C. Corneal (lymph)angiogenesis—from bedside to bench and back: a tribute to Judah Folkman. Lymphat Res Biol. 2008; 6(3-4):191-201. PMID: 19093792
6. Alward W L. Axenfeld-Rieger syndrome in the age of molecular genetics. Am J Ophthalmol. 2000; 130(1):107-15. PMID: 11004268
7. Chang T C, Summers C G, Schimmenti L A, Grajewski A L. Axenfeld-Rieger syndrome: new perspectives. Br J Ophthalmol. 2012; 96(3):318-22. PMID: 22199394
8. Tumer Z, Bach-Holm D. Axenfeld-Rieger syndrome and spectrum of PITX2 and FOXC1 mutations. Eur J Hum Genet. 2009; 17(12):1527-39. PMID: 19513095
9. Seo S, Singh H P, Lacal P M, Sasman A, Fatima A, Liu T, Schultz K M, Losordo D W, Lehmann O J, Kume T. Forkhead box transcription factor FoxC1 preserves corneal transparency by regulating vascular growth. Proc Natl Acad Sci USA. 2012; 109(6):2015-20. PMID: 22171010, PMCID:3277512
10. Anderson C, Zhou Q, Wang S. An alkali-burn injury model of corneal neovascularization in the mouse. J Vis Exp. 2014(86). PMID: 24748032, PMCID:PMC4164081
11. Baulmann D C, Ohlmann A, Flugel-Koch C, Goswami S, Cvekl A, Tamm E R. Pax6 heterozygous eyes show defects in chamber angle differentiation that are associated with a wide spectrum of other anterior eye segment abnormalities. Mech Dev. 2002; 118(1-2):3-17. PMID: 12351165
12. Hill R E, Favor J, Hogan B L, Ton C C, Saunders G F, Hanson I M, Prosser J, Jordan T, Hastie N D, van Heyningen V. Mouse small eye results from mutations in a paired-like homeobox-containing gene. Nature. 1991; 354(6354):522-5. PMID: 1684639
13. Ramaesh T, Collinson J M, Ramaesh K, Kaufman M H, West J D, Dhillon B. Corneal abnormalities in Pax6+/− small eye mice mimic human aniridia-related keratopathy. Invest Ophthalmol Vis Sci. 2003; 44(5):1871-8. PMID: 12714618
14. Morbidelli L, Ziche M. The Rabbit Corneal Pocket Assay. Methods Mol Biol. 2016; 1430:299-310. PMID: 27172962
15. Feizi S, Azari A A, Safapour S. Therapeutic approaches for corneal neovascularization. Eye Vis (Lond). 2017; 4:28. PMID: 29234686, PMCID:PMC5723406
16. Liu X, Wang S, Wang X, Liang J, Zhang Y. Recent drug therapies for corneal neovascularization. Chem Biol Drug Des. 2017; 90(5):653-64. PMID: 28489275
17. Kwon Y S, Kim J C. Inhibition of corneal neovascularization by rapamycin. Exp Mol Med. 2006; 38(2):173-9. PMID: 16672771
18. Murata M, Shimizu S, Horiuchi S, Taira M. Inhibitory effect of triamcinolone acetonide on corneal neovascularization. Graefes Arch Clin Exp Ophthalmol. 2006; 244 (2):205-9. PMID: 16044325
19. Colella P, Ronzitti G, Mingozzi F. Emerging Issues in AAV-Mediated In Vivo Gene Therapy. Mol Ther Methods Clin Dev. 2018; 8:87-104. PMID: 29326962, PMCID: PMC5758940
20. Prosser J, van Heyningen V, PAX6 mutations reviewed. Hum Mutat. 1998; 11(2):93-108
21. Mirzayans I, Pearce W G, MacDonald M, and Walter M A. Mutation of the PAX6 Gene in Patients with Autosomal Dominant Keratitis. Am. J. Hum. Genet. 57:539-548, 1995.
22. Koo, H-Y, and Kume T. FoxC1-dependent regulation of VEGF signaling in corneal avascularity. Trends Cardiovasc Med. 2013 January; 23(1):1-4.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating and/or inhibiting corneal vascularization in a subject in need thereof, the method comprising administering a therapeutic agent to the subject that results in an increase in concentration of FOXC1 in the cornea of the subject than the concentration of FOXC1 in the cornea of the subject prior to administering the therapeutic agent, wherein the therapeutic agent is administered to the surface of the cornea of the subject and the therapeutic agent is an adenovirus-associated viral (AAV) vector that expresses FOXC1 or a variant thereof comprising an amino acid sequence having at least about 80% sequence identity to SEQ ID NO:1, wherein the subject in need thereof does not have FOXC1-attributable Axenfeld-Rieger syndrome.

2. The method of claim 1, wherein the subject has or at risk for developing corneal vascularization from bacterial or viral infection, corneal vascularization from chemical injury, corneal vascularization from an autoimmune response, or corneal vascularization after a corneal transplant.

3. The method of claim 1, wherein the subject has a PAX6 mutation and the subject has or is at risk for developing corneal vascularization due to the PAX6 mutation.

* * * * *

SEQUENCE LISTING

```
<160> NUMBER OF SEQ ID NOS: 2

<210> SEQ ID NO 1
<211> LENGTH: 553
<212> TYPE: PRT
<213> ORGANISM: Homo sapiens

<400> SEQUENCE: 1

Met Gln Ala Arg Tyr Ser Val Ser Ser Pro Asn Ser Leu Gly Val Val
1               5                   10                  15

Pro Tyr Leu Gly Gly Glu Gln Ser Tyr Tyr Arg Ala Ala Ala Ala
            20                  25                  30

Ala Gly Gly Gly Tyr Thr Ala Met Pro Ala Pro Met Ser Val Tyr Ser
            35                  40                  45

His Pro Ala His Ala Glu Gln Tyr Pro Gly Gly Met Ala Arg Ala Tyr
        50                  55                  60

Gly Pro Tyr Thr Pro Gln Pro Gln Pro Lys Asp Met Val Lys Pro Pro
65                  70                  75                  80

Tyr Ser Tyr Ile Ala Leu Ile Thr Met Ala Ile Gln Asn Ala Pro Asp
                85                  90                  95

Lys Lys Ile Thr Leu Asn Gly Ile Tyr Gln Phe Ile Met Asp Arg Phe
            100                 105                 110

Pro Phe Tyr Arg Asp Asn Lys Gln Gly Trp Gln Asn Ser Ile Arg His
            115                 120                 125

Asn Leu Ser Leu Asn Glu Cys Phe Val Lys Val Pro Arg Asp Asp Lys
    130                 135                 140

Lys Pro Gly Lys Gly Ser Tyr Trp Thr Leu Asp Pro Asp Ser Tyr Asn
145                 150                 155                 160

Met Phe Glu Asn Gly Ser Phe Leu Arg Arg Arg Arg Phe Lys Lys
                165                 170                 175

Lys Asp Ala Val Lys Asp Lys Glu Glu Lys Asp Arg Leu His Leu Lys
            180                 185                 190

Glu Pro Pro Pro Gly Arg Gln Pro Pro Ala Pro Pro Glu Gln
            195                 200                 205

Ala Asp Gly Asn Ala Pro Gly Pro Gln Pro Pro Val Arg Ile Gln
    210                 215                 220

Asp Ile Lys Thr Glu Asn Gly Thr Cys Pro Ser Pro Gln Pro Leu
225                 230                 235                 240

Ser Pro Ala Ala Ala Leu Gly Ser Gly Ser Ala Ala Val Pro Lys
            245                 250                 255

Ile Glu Ser Pro Asp Ser Ser Ser Ser Leu Ser Ser Gly Ser Ser
                260                 265                 270

Pro Pro Gly Ser Leu Pro Ser Ala Arg Pro Leu Ser Leu Asp Gly Ala
            275                 280                 285

Asp Ser Ala Pro Pro Pro Ala Pro Ser Ala Pro Pro His His
        290                 295                 300

Ser Gln Gly Phe Ser Val Asp Asn Ile Met Thr Ser Leu Arg Gly Ser
305                 310                 315                 320

Pro Gln Ser Ala Ala Ala Glu Leu Ser Ser Gly Leu Leu Ala Ser Ala
            325                 330                 335
```

```
Ala Ala Ser Ser Arg Ala Gly Ile Ala Pro Pro Leu Ala Leu Gly Ala
            340                 345                 350

Tyr Ser Pro Gly Gln Ser Ser Leu Tyr Ser Ser Pro Cys Ser Gln Thr
            355                 360                 365

Ser Ser Ala Gly Ser Ser Gly Gly Gly Gly Gly Ala Gly Ala Ala
            370                 375                 380

Gly Gly Ala Gly Gly Ala Gly Thr Tyr His Cys Asn Leu Gln Ala Met
385                 390                 395                 400

Ser Leu Tyr Ala Ala Gly Glu Arg Gly Gly His Leu Gln Gly Ala Pro
            405                 410                 415

Gly Gly Ala Gly Gly Ser Ala Val Asp Asp Pro Leu Pro Asp Tyr Ser
            420                 425                 430

Leu Pro Pro Val Thr Ser Ser Ser Ser Ser Leu Ser His Gly Gly
            435                 440                 445

Gly Gly Gly Gly Gly Gly Gly Gln Glu Ala Gly His His Pro Ala
            450                 455                 460

Ala His Gln Gly Arg Leu Thr Ser Trp Tyr Leu Asn Gln Ala Gly Gly
465                 470                 475                 480

Asp Leu Gly His Leu Ala Ser Ala Ala Ala Ala Ala Ala Ala Gly
                    485                 490                 495

Tyr Pro Gly Gln Gln Gln Asn Phe His Ser Val Arg Glu Met Phe Glu
            500                 505                 510

Ser Gln Arg Ile Gly Leu Asn Asn Ser Pro Val Asn Gly Asn Ser Ser
            515                 520                 525

Cys Gln Met Ala Phe Pro Ser Gln Ser Leu Tyr Arg Thr Ser Gly
            530                 535                 540

Ala Phe Val Tyr Asp Cys Ser Lys Phe
545                 550

<210> SEQ ID NO 2
<211> LENGTH: 422
<212> TYPE: PRT
<213> ORGANISM: Homo sapiens

<400> SEQUENCE: 2

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
```

-continued

```
145                 150                 155                 160
Gly Trp Tyr Pro Gly Thr Ser Val Pro Gly Gln Pro Thr Gln Asp Gly
                165                 170                 175
Cys Gln Gln Gln Glu Gly Gly Gly Glu Asn Thr Asn Ser Ile Ser Ser
                180                 185                 190
Asn Gly Glu Asp Ser Asp Glu Ala Gln Met Arg Leu Gln Leu Lys Arg
            195                 200                 205
Lys Leu Gln Arg Asn Arg Thr Ser Phe Thr Gln Glu Gln Ile Glu Ala
        210                 215                 220
Leu Glu Lys Glu Phe Glu Arg Thr His Tyr Pro Asp Val Phe Ala Arg
225                 230                 235                 240
Glu Arg Leu Ala Ala Lys Ile Asp Leu Pro Glu Ala Arg Ile Gln Val
                245                 250                 255
Trp Phe Ser Asn Arg Arg Ala Lys Trp Arg Arg Glu Glu Lys Leu Arg
                260                 265                 270
Asn Gln Arg Arg Gln Ala Ser Asn Thr Pro Ser His Ile Pro Ile Ser
            275                 280                 285
Ser Ser Phe Ser Thr Ser Val Tyr Gln Pro Ile Pro Gln Pro Thr Thr
        290                 295                 300
Pro Val Ser Ser Phe Thr Ser Gly Ser Met Leu Gly Arg Thr Asp Thr
305                 310                 315                 320
Ala Leu Thr Asn Thr Tyr Ser Ala Leu Pro Pro Met Pro Ser Phe Thr
                325                 330                 335
Met Ala Asn Asn Leu Pro Met Gln Pro Pro Val Pro Ser Gln Thr Ser
            340                 345                 350
Ser Tyr Ser Cys Met Leu Pro Thr Ser Pro Ser Val Asn Gly Arg Ser
        355                 360                 365
Tyr Asp Thr Tyr Thr Pro Pro His Met Gln Thr His Met Asn Ser Gln
        370                 375                 380
Pro Met Gly Thr Ser Gly Thr Thr Ser Thr Gly Leu Ile Ser Pro Gly
385                 390                 395                 400
Val Ser Val Pro Val Gln Val Pro Gly Ser Glu Pro Asp Met Ser Gln
                405                 410                 415
Tyr Trp Pro Arg Leu Gln
            420
```